Figure 1:
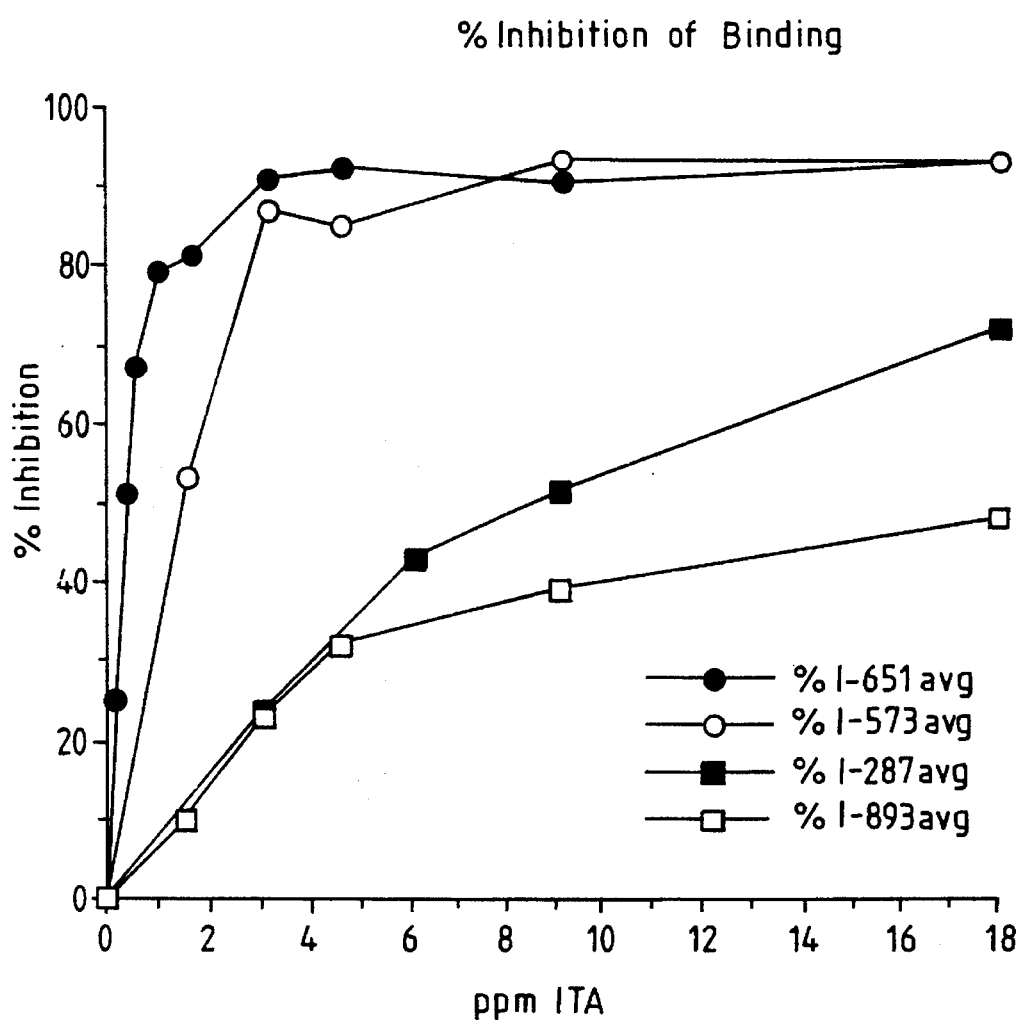

United States Patent [19]

Willingham et al.

[11] Patent Number: 5,554,542

[45] Date of Patent: Sep. 10, 1996

[54] IMMUNOASSAY FOR ISOTHIAZOLONES

[75] Inventors: Gary L. Willingham, Glenside, Pa.; Richard F. Schuman, North Potomac; Chun-Hsien Huang, Rockville, both of Md.; John S. Chapman, Ambler, Pa.

[73] Assignee: Rohm and Haas Company, Philadelphia, Pa.

[21] Appl. No.: 128,451

[22] Filed: Sep. 28, 1993

Related U.S. Application Data

[63] Continuation-in-part of Ser. No. 927,765, Sep. 28, 1992, abandoned.

[51] Int. Cl.⁶ .............. G01N 33/531; C12N 5/20; C07K 16/44
[52] U.S. Cl. .............. 436/548; 436/92; 436/815; 435/240.27; 530/388.9
[58] Field of Search .............. 435/240.27; 436/547, 436/548, 815, 822, 824, 92; 530/402, 403, 388.9, 389.8; 935/95, 102, 103, 104, 105

[56] References Cited

U.S. PATENT DOCUMENTS

| | | | |
|---|---|---|---|
| 4,456,691 | 6/1984 | Stark | 530/389.8 |
| 4,865,972 | 9/1989 | Hunter | 435/7.21 |
| 5,094,957 | 3/1992 | Willingham | 436/92 |

FOREIGN PATENT DOCUMENTS

| | | |
|---|---|---|
| 260829 | 8/1987 | European Pat. Off. . |
| 9203727 | 3/1992 | WIPO . |

OTHER PUBLICATIONS

Nature, vol. 256, pp. 495–497, Kohlu et al.
Journal of Applied Bacteriology, 1990, 69:578–584 Collier et al.
Proclin 300™ product bulletin, Rohm and Haas Co., Philadelphia, PA.
Toxicology and Applied Pharm., 50, pp. 137–146 (1979), Albeo et al.
The Journal of Cell Biology, vol. 93, Jun. 1982, pp. 576–582 Kilmartin et al.
Science, 210:537 (1980) Nowinski et al.
FEBS Letter, 149: 147–151 (1982) Hunter et al.
Sudi et al., Kieler Milchwictshaftliche for Schungsberichte 40 (3) 1988, pp. 179–203.

*Primary Examiner*—Esther M. Kepplinger
*Assistant Examiner*—Lora M. Green
*Attorney, Agent, or Firm*—Michael B. Fein

[57] ABSTRACT

Immunoassay for isothiazolones based on monoclonal antibodies that react with isothiazolones, particularly, 5-chloro-2-methyl-3-isothiazolone, hybridomas that produce such antibodies, especially ATCC HB 11435, a method of preparing an immunogenic conjugate of isothiazolones and a macromolecule carrier, a method of producing monoclonal antibodies reactive with isothiazolones, and compositions comprising monoclonal or polyclonal antibodies reactive with isothiazolones.

5 Claims, 1 Drawing Sheet

IMMUNOASSAY FOR ISOTHIAZOLONES

This is a continuation-in-part of U.S. application Ser. No. 07/927,765, filed Sep. 28, 1992 abn.

I. BACKGROUND OF THE INVENTION

A. Field of the Invention

This invention relates to methods of detection of low concentrations of isothiazolone compounds using immunoassays.

B. Description of the Prior Art

Isothiazolone compounds are widely used as biocides in many applications where water or moisture is present. In many of those applications, there is a need to determine the proper dosage and stability of the isothiazolone in the system. The present state of the art is to use HPLC analytical methods which are time consuming, inconvenient, and expensive.

Westinghouse Electric Corporation European Patent Application Number 0260829, published Mar. 23, 1988 (inventor: Kenneth W. Hunter) disclosed monoclonal antibodies which react with chlorinated phenols, particularly pentachlorophenol, and hybridomas which produce such antibodies; and an immunoassay for such chlorinated phenols. Although detection methods for many compounds would benefit greatly by development of an immunoassay, appropriate cell lines are very difficult to create.

U.S. Pat. No. 4,865,972 (Hunter) discloses an antibody based assay for enzyme-inducing chemicals (such as dibenzodioxins). Isothiazolones are not enzyme-inducing compounds.

Kohler and Milstein, Nature 265:495 (1975), first described how monoclonal antibodies directed to sheep red blood cells may be prepared by fusing a specific antibody-producing B-lymphocyte with a tumor cell, resulting in an "immortal" self-reproducing hybrid clone (or "hybridoma") that can synthesize, in a cell culture (in vitro.) or an animal (in vivo), a single, monoclonal antibody.

II. SUMMARY OF THE INVENTION

It was an object of the present invention to develop an improved method of detecting isothiazolone compounds.

A further object was to create a cell line which would be useful in an immunoassay method for detecting isothiazolones.

These objects and others which will become apparent from the following disclosure are achieved by the present invention which comprises in one aspect a new cell line which produces monoclonal antibodies reactive with 3-isothiazolones, especially 5-chloro-2-methyl-3-isothiazolone. This invention also relates to monoclonal and polyclonal antibodies that react with such isothiazolones. The invention is directed to the antibodies, processes of preparing the antibodies, analytic, diagnostic, investigational, separatory, and the other methods of using the antibodies, and compositions containing the antibodies for such uses. In addition, the invention is directed to hybridomas that produce the monoclonal antibodies and to methods of making the hybridomas. Finally, the invention is directed to immunogenic conjugates of isothiazolones and a macromolecule carrier and to methods of making such conjugates. dr

III. BRIEF DESCRIPTION OF THE DRAWINGS

FIG. 1 is a graph showing the percent inhibition of binding of four different species of isothiazolones of a immunoassay according to the invention.

IV. DETAILED DESCRIPTION OF THE INVENTION AND THE PREFERRED EMBODIMENTS

The isothiazolones as a class are very reactive electrophiles having a first order rate constant for reaction with thiols of $1.053 \times 10^3$ mol/sec (P. J. Collier et al., J. Appl. Bacteriol., 69:578–584, 1991). Also, 5-chloro-2-methyl-3-isothiazolone has the capability of reacting further after the ring-opening reaction with thiols. It is well know that blood sera and red blood cells contain high levels of glutathione, a reduced thiol compound. Immediately after the introduction of isothiazolones into bovine serum, the isothiazolones are non-detectable by either bioassay, ultraviolet spectroscopy or high performance liquid chromatography (Proclin® 300 product bulletin, Rohm and Haas Company, Philadelphia, Pa.), implying the reaction of isothiazolone with a nucleophile and the destruction of the intact ring structure. This demonstrated rapid reaction of isothiazolones with nucleophiles known to be present in sera would lead one to predict that an intact isothiazolone introduced into an animal for the purpose of inducing antibody formation would not survive intact long enough to interact with the appropriate elements of the immune system. It is therefore quite unexpected that antibodies to isothiazolones can be induced.

We have discovered novel antibodies which satisfy a number of critical needs not fulfilled by existing analytical technology. Such antibodies allow the detection of biocide by a variety of rapid, simple, and cost effective immunoassay techniques. The novel antibodies are particularly useful for analyzing the isothiazolone compound in water, since the isothiazolone does not have to be extracted first.

The use of polyclonal antibodies is possible, but the use of monoclonal antibodies is highly preferred. Monoclonal antibodies are derived from a single B-lymphocyte clone ("hybridoma") which makes them very specific and homogeneous. Such a hybridoma is, in fact, a self-reproducing cell "factory" which can produce a potentially limitless supply of an antibody with single, pre-defined specificity.

While the monoclonal antibody of the present invention was developed against 2-methyl-3-isothiazolone ("573"), it has cross-reactivity with other isothiazolones, for example, 5-chloro-2-methyl-3-isothiazolone ("651"), 4,5-dichloro-2-n-octyl-3-isothiazolone ("287"), and 2-n-octyl-3-isothiazolone ("893") as shown in FIG. 1.

The isothiazolones useful with this invention are of the formula

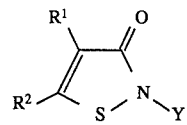

wherein $R^1$ and $R^2$ are independently selected from hydrogen, halogen or a ($C_1$–$C_4$) alkyl group or alternatively may be joined to form a saturated, unsaturated or aromatic 5- or 6-membered fused carbocyclic ring; Y is hydrogen, an unsubstituted or halo-substituted ($C_1$–$C_{18}$) alkyl group, an unsubstituted or halo-substituted alkenyl or alkynyl group of 2 to 8 carbons, an unsubstituted or halo-substituted ($C_3$–$C_8$) cycloalkyl, an aralkyl or halo-, ($C_1$–$C_4$) alkyl-, or ($C_1$–$C_4$) alkoxy-substituted aralkyl of up to 10 carbon atoms, or an aryl or halo-, ($C_1$–$C_4$) alkyl-, or ($C_1$–$C_4$) alkoxy-substituted aryl group of up to 10 carbon atoms.

Representative Y substituents include methyl, ethyl, propyl, isopropyl, butyl, hexyl, octyl, cyclohexyl, 4-methoxyphenyl, 4-chlorophenyl, 3,4-dichlorophenyl, benzyl, 4-methoxybenzyl, 4-chlorobenzyl, phenethyl, 4-phenylbutyl, chloromethyl, chloropropyl, hydrogen and the like.

The monoclonal antibodies are made by producing an immunogenic conjugate of the isothiazolones and a macromolecule carrier, immunizing an animal with the conjugate, obtaining antibody-producing cells from the animal, fusing the cells with tumor cells to produce hybridomas, selecting from among the hybridomas at least one that produces antibodies reactive with isothiazolones, and recovering the produced antibodies from the selected hybridoma.

An in vivo method of producing monoclonal antibodies reactive with isothiazolones involves intraperitoneally placing in a histocompatible or immunosuppressed host a hybridoma that produces such antibodies and recovering the produced antibodies from the ascites fluid of the host. A continuous cell line that produces monoclonal antibodies to isothiazolones is prepared by producing an immunogenic conjugate of the isothiazolones and a macromolecule carrier, immunizing an animal with the conjugate, obtaining antibody producing cells from the animal, fusing the antibody-producing cells with tumor cells to produce hybridomas, selecting from among the hybridomas a hybridoma that produces antibodies reactive with the isothiazolones, and clonally expanding the selected hybridoma into a cell line. The antibodies produced by the continuous cell line selected are referred to as "anti-651" antibodies.

To detect the presence or concentrations of isothiazolones in a sample, monoclonal antibodies reactive with the isothiazolones are added to the sample and the presence or concentrations of the isothiazolones is determined by an immunoassay wherein the monoclonal antibodies are used as a reagent.

The monoclonal antibodies are preferably provided in an acceptable carrier.

The anti-651 antibody can be coupled to the enzyme horseradish peroxidase ("HRP") using standard procedures. This coupled enzyme-antibody can be used as an immunological stain to determine the location of isothiazolones in solid matrices such as wood, leather and plastics. The matrix to be examined is sectioned into thin slices by an appropriate method, and then incubated with the coupled enzyme-antibody for a period of time, during which it reacts with the isothiazolone or isothiazolones. After incubation, the unbound enzyme-antibody is removed by washing with buffer, such as PBS-Tween. Next, the treated matrix material is incubated with enzyme substrate, of which a number of commercially available chromogenic compounds are available. The matrix is treated with the substrate in such a volume that the colored product does not diffuse away from the site of reaction. Alternatively, the substrate may be incorporated into a membrane which is overlaid on the treated substrate. An example of such a product is the Enzygraphic Web from International Biotechnologies Inc. ("IBZ"). The isothiazolone is localized by visual or microscopic examination of the matrix, or of the substrate-impregnated membrane.

An alternative to the use of enzyme coupled antibody is the use of ferritin or gold-labelled antibody, or the use of radio-labelled antibodies. Radio-labelled antibodies require the exposure of the treated matrix to photographic film.

The antibody can also be used to determine the presence and concentration of isothiazolones in a solid matrix, such as wood, plastic or leather. The solid matrix can be tested for the presence of isothiazolone by soaking wafers of the matrix in a solution of a protein blocking agent, such as nonfat milk or Bovine Serum Albumin ("BSA"), for 30–60 minutes. The wafers are then rinsed briefly with PBS-Tween (PBS-T) buffer, and exposed to the anti-651 antibody, which is covalently linked to horseradish peroxidase, for 15 minutes. The wafers are then washed twice for a period of time each in PBS-T buffer. The bound anti-651-HRP complex can then be visualized by placing the wafers in a vial containing HRP substrate, such as ABTS (2,2'-azino-bis-3-ethylbenzthiazolin-6-sulfonic acid). Alternatively, the enzyme substrate can be placed on the surface of the wood either as a solution or as a substrate affixed to a solid support, such as the commercially available Enzygraphic Web (IBI). The appearance of a color indicates the presence of isothiazolone and the intensity of the color relates to the concentration of the isothiazolone.

An immunological procedure can be employed for the isolation or removal of isothiazolones from a mixture on the basis of a selective immunological reaction in which a monoclonal antibody reactive with the isothiazolones is used as the antibody.

A composition for isolating or removing an isothiazolone compound from a mixture containing said compound comprises an effective amount of monoclonal antibody reactive with the isothiazolone compound, immobilized on a matrix or in admixture with a carrier.

Polyclonal antibodies reactive with isothiazolone compound are produced by producing an immunogenic conjugate of the isothiazolone and a macromolecule carrier, immunizing an animal with the conjugate, removing blood from the animal, separating the serum from the blood, and recovering the antibodies from the serum.

An immunogenic conjugate comprising isothiazolone compound covalently bonded to a macromolecule carrier are produced by covalently attaching a chemical linker to the macromolecule carrier and covalently attaching a derivative of the isothiazolone, such derivative containing a reactive group, to the chemical linker, thereby forming the immunogenic conjugate.

In a particularly preferred embodiment, the monoclonal antibodies of the present invention have the characteristics of the monoclonal antibodies produced by the hybridoma cell line ATCC HB 11435 or mutants or variants thereof. ATCC HB 11435 is a biologically pure culture available from the Patent Depository of the American Type Culture Collection (ATCC), 12301 Parklawn Drive, Rockville, Md. U.S.A. 20852 and was deposited on May 10, 1991 and was transferred to the Patent Depository on Aug. 13, 1993 under the reference B9 -147EH9-IIIH6 alter having met tin requirements of the Budapest Treaty. ATCC HB 11435 was produced by fusion of a mouse B-lymphocyte and a mouse plasmacytoma cell. The immunoglobulins (antibodies) produced by these hybridomas are of the IgG class. The monoclonality of ATCC HB 11435 antibodies was insured by re-cloning the hybridomas which produced them.

The monoclonal antibodies produced by ATCC HB 11435 will prevent other monoclonal antibodies that would otherwise react with 5-chloro-2-methyl- 3-isothiazolone, which have been produced by other hybridomas, from so reacting.

The hybridomas and continuous cell lines can be prepared by:

(a) producing an immunogenic conjugate of a macromolecule carrier and the particular isothiazolones to which a monoclonal antibody is sought;

(b) immunizing an animal with the conjugate;

(c) obtaining antibody-producing cells from the animal;

(d) fusing the antibody-producing cells with tumor cells to produce hybridomas;

(e) screening from among the hybridomas a hybridoma that produces antibodies reactive with the immunogenic conjugates produced in step (a) supra; to produce a cell line (f) screening from among the hybridomas a hybridoma which produces antibodies reactive with free isothiazolones; and (g) cloning.

The monoclonal antibodies can be recovered from the selected hybridoma or hybridomas before or after they are expanded by cloning into a continuous cell line.

Alternatively, cells other than spleen cells can be used to produce antibodies to isothiazolones. The hybridomas produced by this embodiment can be used to produce the monoclonal antibodies of the invention by culturing them in a suitable medium and recovering the antibodies from the medium.

Substances with molecular weights of approximately 1,000 or less, such as 5-chloro-2-methyl-3-isothiazolone (molecular weight 152), do not ordinarily induce the production of antibodies, i.e., they are non-immunogenic. However, such substances often can be chemically attached to larger, immunogenic carrier molecules, such as a carbohydrate or a protein, in order to induce the production of antibodies against the smaller substance, which is known as a hapten. The general techniques for producing an immunogenic conjugate of a hapten and a macromolecule carrier are known in the art. For example, see U.S. Pat. No. 4,456,691 to Stark, issued Jun. 26, 1984 and Albro et al., *Toxicol Appl. Pharmacol*, 50. 137–146 (1979).

The methods of Albro et al. and Stark involve covalently bonding the hapten to the macromolecule carrier through a chemical bridge or linker. The chemical linker is a bifunctional molecule that contains reactive groups on opposite ends. The reactive groups allow the chemical linker to react with reactive groups on the macromolecule and on the hapten so that one end of the chemical linker is covalently bonded to the hapten. The chemical linker is added first to the hapten and the resulting compound is then added to the macromolecule carrier through the reactive group at the other end of the chemical linker.

It is known that antibodies raised against small chemical compounds conjugated to carrier proteins tend to recognize not only the structure of the chemical, but also the structures of the linker between chemical and protein, and even structures on the protein adjacent to the site of attachment of the linker. The results of such recognition of ancillary structures is the inability, or markedly reduced ability, of the antibody to bind to the free chemical. This is particularly a problem for monoclonal antibodies. This problem must be overcome if monoclonal antibodies to chemicals are to be useful for quantitative analysis. Surprisingly, we have discovered antibodies which perform this function with isothiazolone compounds, solving a long-felt need in the art.

Once the immunogenic conjugate has been produced, it is used to immunize an animal host known by techniques. Such techniques usually involve inoculation, but they may involve other modes of administration. A sufficient amount of the conjugate is administered to create an immunogenic response in the animal host.

Any host that produces antibodies to the conjugate may be used. Conventionally used animals include rabbits and rodents, such as rats or mice. Mice and rats are preferred for the present invention.

Once the animal has been immunized and sufficient time has passed for it to begin producing antibodies to the conjugate, polyclonal antibodies may be recovered by techniques known in the art. The general method comprises removing blood from the animal and separating the serum from the blood. The serum, which contains antibodies to the isothiazolones used as the hapten in the preparation of the conjugate, may be used as an antiserum to the isothiazolones. Alternatively, the antibodies can be recovered from the serum. Affinity purification is a preferred technique for recovering purified polyclonal antibodies to isothiazolones from the serum.

Monoclonal antibody-producing cells are recovered from the immunized animal. Although any antibody-producing cells may be used, B-lymphocytes obtained from the animal's spleen are preferred.

The antibody-producing cells are fused with tumor cells to produce hybridomas. As used herein, the term "tumor cell" includes any cell that is capable of fusing with an antibody-producing cell to create a hybrid "immortal" cell, i.e., one which is capable of continuous growth in vitro. Preferred tumor cells are antibody-producing cells which have been transformed and which have lost their ability to produce immunoglobulin. Such cells include rat myeloma cells and mouse plasmacytoma cells. Particularly preferred are mouse plasmacytoma cells or rat myeloma cells that are deficient in the enzyme hypoxanthinequanine phosphoribosyl transferase (HGPRT), which allows the selection of hybridomas from unfused antibodying-producing cells or plasmacytoma or myeloma cells when grown on a medium containing hypoxanthine, aminopterin and thymidine.

Various tumor cells useful for fusing with antibody-producing cells are known and readily available. One such type of cell is the mouse plasmacytoma cell line P3-X63-Ag8.653., described in Kearney, *J. Immunology*, 123. 1548 (1979). Another cell line is the rat myeloma cell line YB2.0, described in Milstein, *J. Cell Biology*, 93:576–582 (1982). These cell lines are available from American Type Culture Collection, Rockville, Md., where they are designated ATCC CRL 1580 and ATCC CRL 1662 respectively.

It should be noted that the antibody-producing cell and the tumor cell can be from different animal species. For example, see Nowinski, et al. *Science*, 210:537 (1980).

As mentioned previously, once the cells have been fused, it is necessary to separate the hybridomas from the unfused cells. The antibody-producing cells will normally die after a few days in culture, but the tumor cells are "immortal." However, by using tumor cells that are deficient in HGPRT and growing the fused cells on a medium containing hypoxanthine, aminopterin, and thymidine, the hybridomas will be naturally selected since the tumor cells are unable to survive on such a medium. However, other known selection techniques may also be used.

After the hybridomas are selected, they are evaluated to determine which are producing antibodies to the isothiazolones. Various immunoassays known to those skilled in the art may be used to evaluate the culture supernatants of the hybridomas. Care must be taken to identify hybridomas that are producing monoclonal antibodies only to the isothiazolones rather than to the isothiazolone-macromolecule carrier. That is, the monoclonal antibodies which are desired, useful, and provided by this invention are those that react with free, i.e., unconjugated or unbound isothiazolones.

The preferred selection technique is an initial screen by an enzyme immunoassay (EIA) to identify hybridomas producing antibodies to the conjugate or to the isothiazolones. These hybridomas are then screened by a competitive inhibition enzyme immunoassay (CIEIA) that evaluates the ability of a free isothiazolone, such as 5-chloro-2-methyl-3-isothiazolone, to inhibit the binding of monoclonal antibodies to the isothiazolone/protein carrier. The CIEIA is conducted according to the method disclosed in Hunter, et al., *FEBS Lett.* 149:147–151 (1982).

Once the monoclonal antibody-producing hybridomas have been selected, the antibodies can be recovered from such hybridomas by known techniques. Generally, it is useful to clone one or more of the monoclonal antibody-producing hybridomas to expand it into a continuous cell line that can be used to produce the monoclonal antibodies in quantity.

The previously mentioned methods of producing the monoclonal antibodies are in vitro methods. An in vivo process for producing monoclonal antibodies to isothiazolones includes placing a hybridoma that produces the antibodies intrapentoneally in a histocompatible or immunosuppressed host. This causes the host to produce ascites tumors which, in turn, produce a fluid that contains the monoclonal antibodies produced by the hybridoma. After a sufficient time has passed for the antibodies to have been produced in sufficient quantities, they may be recovered by known techniques. For example, the ascites fluid may be removed and the monoclonal antibodies recovered in pure form by affinity purification. This method is particularly suitable for producing the monoclonal antibodies in commercially useful quantities.

Just as a variety of different systems and methods might be employed to produce monoclonal antibodies reactive with isothiazolones, so do a variety of monoclonal antibodies result from these measures that are distinct from the antibody illustrated in the Examples below. However, such monoclonal antibodies, whose production is enabled by the teachings therein, are still clearly within the scope of this invention. This salient feature of such antibodies, for the purposes of this invention, besides their monoclonality, is their reactivity in any way with isothiazolones, regardless of the species of origin, isotype, molecular specificity, affinity, method of production, or particular type of hybridoma employed in their production.

The monoclonal and polyclonal antibodies can be used to identify isothiazolones, particularly 5-chloro-2-methyl-3-isothiazolone, in materials and to determine the concentration of the chemical in those materials. Such materials include, for example, soil, water, food, and body fluids. When used as a reagent in various immunoassays for determining the presence of concentration of isothiazolones, the antibodies of the present invention provide an improved assay. Detection is convenient, rapid, sensitive, and specific. The immunoassays in which the antibodies of the present invention may be used include, but are not limited to, radioimmunoassay, competition immunoprecipitation assay, enzyme-linked immunoabsorbent assay, and immunofluorescence assay. The monoclonal antibodies of the present invention are generally the preferred antibodies, although the polyclonal antibodies are preferred in certain applications.

A composition for determining the presence or concentration of isothiazolones in material contains a concentration of antibodies to the chemical effective to detect the presence of the chemical or to quantify its amount. The antibodies can be mixed with or attached to any suitable carrier, such as a latex particle or plastic microtiter plate. They may also be conjugated with an enzyme or dye or radio-labelled, depending upon what immunological method is employed. Consequently, any assay system which employs monoclonal or polyclonal antibodies with isothiazolones, including 5-chloro-2-methyl-3-isothiazolone, is embraced by this invention.

The monoclonal and polyclonal antibodies are also useful for the isolation, purification, neutralization, and/or removal of isothiazolones from complex mixtures of solutions on the basis of a selective immunological reaction. The use of antibodies reactive with isothiazolones represents an improvement over the known methods.

Monoclonal antibodies are preferred over polyclonal antibodies. Because of their great specificity and their availability in virtually limitless quantities, monoclonal antibodies can be used on a large industrial or commercial scale. For example, anti-651 antibodies are useful to separate and purify 5-chloro-2-methyl-3-isothiazolone from a mixture of other isothiazolones or similar organic compounds. The mixture is brought into contact with immobilized monoclonal antibodies to 5-chloro-2-methyl-3-isothiazolone, which separates the 5-chloro-2-methyl-3-isothiazolone from the mixture by forming immobilized complexes of the 5-chloro-2-methyl-3-isothiazolone bound to the antibody. After the mixture is removed, the 5-chloro-2-methyl-3-isothiazolone is separated from the antibodies and recovered in purified form by known techniques.

A composition useful for purifying or removing isothiazolones from complex mixtures contains an effective amount of the monoclonal antibody immobilized on an acceptable matrix or in admixture with an acceptable carrier, to permit reaction and binding with isothiazolones. However, for certain mixtures, polyclonal antibodies may be preferred.

The monoclonal antibodies of this invention are also useful reagents for research related to the structure and function of isothiazolones, particularly 5-chloro-2-methyl-3-isothiazolone. Their exquisite specificity allows them to be used for immunochemical and structure-activity analyses of these chemicals, and makes them more useful in these applications than less specific polyclonal antibodies.

The compositions are useful as investigational reagents.

The following non-limiting examples illustrate a few embodiments of the invention.

EXAMPLES

Example 1—Synthesis of the Immunizing Conjugates

Thionyl chloride (71.38 g, 0.6 mol) and pyridine (0.5 ml) were added to 3,3'-dithiodipropionic acid (21.03 g, 0.1 mol) with external cooling. This mixture was stirred at room temperature overnight. The excess thionyl chloride was removed in vacuo to yield 3,3'-dithiodipropionyl chloride as a light amber oil (23.7 g, 100% yield) which was used in the next step without purification.

A mixture of methyl 4-aminobutyrate·HCl (37.2 g, 0.242 mol) and triethylamine (67.8 ml, 0.486 mol) in ethylene dichloride (EDC, 300 ml) was stirred for 30 minutes at room temperature. The 3,3'-dithiodipropionyl chloride was dissolved in 50 ml EDC and added dropwise with cooling to the stirred solution, maintaining the temperature at approximately 25° C. The mixture was allowed to stir at room temperature overnight. The mixture was then poured into water and the organic layer separated. The organic layer was then washed with saturated $NaHCO_3$ solution, water, and then brine. The solution was then dried and concentrated to give a semi-solid brown residue. This residue was triturated in ethyl acetate with cooling to give 3,3'-dithio-di-N-(3-methoxycarbonylpropyl)propionamide (compound I) as an off-white solid which was filtered and dried (20.4 g).

Compound I was cyclized to the isothiazolone. 3,3'-Dithio-di-N-(3-methoxycarbonylpropyl)propionamide (12.0 g, 0.029 mol) and sulfuryl chloride (19.8 g, 0.147 mol) were charged concurrently over a one hour period to a flask containing cooled (0° C.) and stirred ethyl acetate (120 ml). The amide and sulfuryl chloride were charged in 24 equal portions of 0.5 g and 0.5 ml respectively every 2.5 minutes.

During the course of the addition, a precipitate formed. After addition was complete, the mixture was stirred at 0° C. for 30 minutes and then allowed to warm to room temperature. The mixture was stirred for one hour at room temperature, cooled to 0° C. and filtered. The solid was dissolved in water and extracted with CHCl$_3$. The CHCl$_3$ layer was washed with water and then brine. Once the CHCl$_3$ was dried, the solvent was removed to yield 5-chloro-2-(3-methoxycarbonylpropyl)-3-isothiazolone as a white solid (yield 8.9 g, m.p. 54°–6° C.).

To prepare 2-(3-methoxycarbonylpropyl)-3-isothiazolone, Compound I (1.02 g, 2.5 mmol) was dissolved in 25 ml distilled ethyl acetate and cooled to 0° C. Sulfuryl chloride (1.04 g, 7.75 mmol) was added slowly dropwise and the yellow solution stirred at 0° C. for 1 hr. During this time a white precipitate formed (5-chloro-2-(3-methoxycarbonylpropyl)-3-isothiazolone (200 mg)) which was removed by filtration. The resulting filtrate was concentrated and the residue flash-chromatographed (10% acetone-chloroform) to yield 2-(3-methoxycarbonylpropyl)- 3-isothiazolone (120 mg) as a clear oil.

The methyl ester of the isothiazolones were hydrolyzed to the free acids. 5 -Chloro-2-(3-methoxycarbonylpropyl)-3-isothiazolone (4.0 g) was taken up in 6 ml of acetic acid. To this stirred solution at room temperature was added 6M aqueous HCl (7 ml). This solution was then stirred at room temperature for 24 hours, during which time a white precipitate formed. The solution was filtered and the filtrate further concentrated to yield more of the same precipitate (5-chloro-2-(3-hydroxy-carbonylpropyl)- 3-isothiazolone). The combined yield was 2.95 g (m.p. 158°–161° C.).

2-(3-Methoxycarbonylpropyl)-3-isothiazolone was dissolved in a solution of 4 ml glacial acetic acid and 2 ml 6N hydrochloric acid. This was stirred at 85° C. for 1 hr. The solution was concentrated in vacuuo and the residue partitioned between water and ethylacetate twice. The ethyl acetate layers were combined, dried and concentrated. The resulting solid was recrystallized from ethyl acetate to give a light yellow powder.

The free acid isothiazolones were then coupled to bovine serum albumin ("BSA") and thyroglobulin ("THY"). 5-Chloro-2-(3-hydroxycarbonylpropyl)-3-isothiazolone (0.45 g, 0.002 mol) and n-Bu$_3$N (0.95 g, 0.0051 mol) were added to dioxane (5 ml). To this stirred suspension was added isobutylchloroformate (0.77 g, 0.0056 mol) dropwise at 0° C. Upon addition of the isobutylchloroformate, the suspended material dissolved. This solution was stirred at room temperature for 1 hour. This yielded the isothiazolone-isobutylformate mixed anhydride which was used without isolation. BSA was dissolved in deionized water (20 ml), followed by addition of a small amount of dioxane (1 ml). To this stirred BSA solution at 0° C. was added dropwise the isothiazolone-isobutylformate mixed anhydride solution. The rate of addition was such that the reaction temperature was maintained at 0° C. After the addition was complete, the mixture was stirred at 0° C. for one hour and then allowed to warm to room temperature, followed by stirring at room temperature for one hour. The mixture was then transferred to a dialysis bag and dialyzed for 24 hours and then lyophilized to remove water. A light, white powder (651-BSA conjugate) was obtained (2.9 g). The conjugates of 651 to THY (651-THY), 573 to BSA (573-BSA), and 573 to THY (573-THY) were prepared in a similar manner.

Example 1A—Immunizations

BALB/c mice were obtained from Taconic Farms, New York, U.S.A., and immunized with 651-BSA, 651-THY, 573-BSA or 573-THY conjugates produced in the previous Example according to the schedule set forth in Table I in which CFA is "Complete Freund's Adjuvant," IFAM "Incomplete Freund's Adjuvant," PBS is "Physiologically Buffered Saline," "sc" is subcutaneous, and "ip" is intraperitoneal.

TABLE IA

| Day | Date | Amount | Adjuvant | Route |
| --- | --- | --- | --- | --- |
| 1 | 12/7/88 | 300 ug | CFA | sc |
| 63 | 2/8/89 | 150 ug | IFA | sc |
| 119 | 4/5/89 | 100 ug | IFA | sc |
| 314 | 10/17/89 | 100 ug | IFA | sc |
| 403 | 1/14/90 | 50 ug | IFA | sc |
| 499 | 4/20/90 | 30 ug | PBS | ip |
| 499 | 4/20/90 | 20 ug | PBS | sc |
| 573 | 7/3/90 | 100 ug | PBS | ip |

Example 1B—Screening for Isothiazolone Anti-Sera

Blood samples were taken from the mice immunized in the above example. The sera were separated from the red blood cells by centrifugation. The sera were then screened for activity using competitive inhibition ELISA (CIEIA). Ninety-six well polystyrene EIA (enzyme inhibition assay) plates were coated with 100 µl of 651 conjugated to BSA (651-BSA), 651 conjugated to THY (651-THY), 573 conjugated to BSA (573-BSA), or 573 conjugated to THY (573-THY) for at least two hours at room temperature or 16 hours at 4° C. Unbound material was washed from the wells with five washes of PBS-T. The wells then received 50 µl of buffer alone (PBS-T) or inhibitors, either 651 or 573, each diluted to 2 ppm in buffer. The wells then received 50 µl of mouse serum, so that each serum was reacted with either buffer, 651 or 573 (inhibitors). The combination of equal volumes of sera and inhibitors or buffer resulted in a final concentration of inhibitors of 1 ppm. The wells were incubated for 30–60 minutes at room temperature. They were then washed five times with PBS-T to remove unbound material and each well then received 100 µl of a 1 µg/ml solution of biotinylated horse anti-mouse IgG (Vector Laboratories, Burlingame, Calif.), and the assay continued as described for the ELISA, supra.

If the antibodies in a serum were reactive with one or both of the inhibitors in solution in the wells, the antibody molecules, or a percentage of the antibody molecules, would bind to the inhibitors, and would therefore form an antibody-inhibitor complex which would stay in solution and be removed from the plate during the washing step. In such a case, the binding of the antibody to the inhibitor would reduce the number of antibody molecules available to bind to the coating antigen, 651-BSA. Because fewer antibody molecules are attached to the 651-BSA, there is a reduction in the number of biotinylated horse anti-mouse IgG molecules bound, resulting in fewer molecules of avidin-peroxidase complex being bound, resulting in reduced hydrolysis of the substrate, leading ultimately to lower absorbances. The data are shown in Table 1A. In all cases, the inhibitor concentration was $10^{-4}$M.

TABLE IB

| Mouse Number | Immunogen | Coating Conjugate | % Inhibition with 651 | % Inhibition with 573 |
|---|---|---|---|---|
| 2A | 651-BSA | 651-THY | 6 | 0 |
| 2A | " | 573-THY | 0 | 0 |
| 3A | " | 651-THY | 0 | 0 |
| 3A | " | 573-THY | 0 | 0 |
| 1B | 651-THY | 651-BSA | 0 | 0 |
| 1B | " | 573-BSA | 0 | 0 |
| 2B | " | 651-BSA | 0 | 0 |
| 2B | " | 573-BSA | 0 | 0 |
| 1C | 573-BSA | 651-THY | 6 | 7 |
| 1C | " | 573-THY | 0 | 0 |
| 2C | " | 651-THY | 0 | 18 |
| 2C | " | 573-THY | 14 | 4 |
| 1D | 573-BSA | 651-THY | 10 | 0 |
| 1D | " | 573-THY | 0 | 12 |
| 2D | " | 651-THY | 12 | 0 |
| 1E | 573-THY | 651-BSA | 34 | 28 |
| 1E | " | 573-BSA | 44 | 21 |
| 2E | " | 651-BSA | 7 | 12 |
| 2E | " | 573-BSA | 12 | 10 |

These results indicate that mouse 1E, immunized with 573-THY, produced serum with antibodies reactive toward both 651 and 573.

Example 2—Fusion

All techniques were performed aseptically and with sterile reagents. Mouse, 1E, producing polyclonal antibodies was killed by excess anesthesia (Rompum®/Ketamine®). The spleen was removed and placed in a 100 mm Petri dish containing approximately 20 ml of ABC medium (Cell Enterprises, Harrisonburg, Va.). The spleen was then perfused with 10 ml of ABC medium to remove most of the splenocytes. The remaining cells were obtained by teasing apart the spleen capsule with 21 gauge needles. The volume was brought to approximately 50 ml with ABC medium and a 0.1 ml sample was removed and diluted 1:50 in ABC medium. The diluted cells were counted on a hemocytometer to obtain an approximation of the number of lymphocytes obtained from the spleen. During this time, the cells were pelletted by centrifugation at approximately 200×g for 5 minutes at room temperature.

Approximately, $1.2 \times 10^8$ lymphocytes were obtained from the spleen. These were mixed with $1.2 \times 10^7$ myeloma cells (SP2/0-Ag14, ATCC Cat CRL1581). The cells were again pelletted by centrifugation (approximately 250×g for 10 minutes at room temperature). The supernatant was removed to near dryness and the cells resuspended by gently tapping the centrifuge tube to loosen the cell pellet.

The cells were then treated with 1 ml of 50% polyethylene glycol, mw 1500 (PEG), which had been prewarmed to 36° C. The PEG was added slowly (dropwise) over a period of approximately 75 seconds, with constant rotating of the centrifuge tube to insure that the cells remained well mixed while in contact with PEG.

The centrifuge tube containing the cells was then placed in a 37° C. water bath for 1 minute. The tube was then removed from the water bath and 1 ml of warm ABC medium was added dropwise during the next 60–75 seconds with constant rotating of the centrifuge tube to insure that the cells and PEG were well mixed with the medium. The cells were again transferred to the 37° C. water bath for 1 minute and then removed from the water bath. Over the next 60–75 seconds, 2 ml of ABC medium were added with constant rotating of the centrifuge tube as before, and the cells transferred again to the 37° C. water bath for 1 minute. The centrifuge tube was removed from the water bath, and 4 ml of warm ABC medium were added, constantly rotating of the centrifuge tube as before. The cells were allowed to incubate for 1 minute at room temperature, after which 8 ml of warm ABC medium were added, constantly rotating of the centrifuge tube as before. The cells were allowed to incubate for 1 minute at room temperature, after which 12 ml of warm ABC medium were added with constant rotating of the centrifuge tube as before. Finally, the volume was brought to approximately 50 ml by addition of ABC medium.

The cells were pelletted by centrifugation as described above. The medium was removed by aspiration and the cells resuspended in 60 ml of HM. These cells were then divided into two 30 ml aliquots, one receiving endothelial cell growth supplement (ECGS (available from Sigma, catalog #E2759), 5 ug/ml) and the other receiving no further supplements.

Cells were plated into 96 well dishes, 100 μl/well. Dishes labelled A,B,C received cells without ECGS; those with ECGS were in dishes labelled D,E,F. The cells were incubated in a humidified atmosphere of 5% $CO_2$ in air.

On day one after fusion, each well received 100 μl of 1×HAT medium, prepared in HM with or without ECGS as appropriate. (HAT is a mixture of hypoxanthine, aminopterin and thymidine. The final concentrations used in the culture medium are $5 \times 10^{-3}$M hypoxanthine, $2 \times 10^{-5}$M aminopterin and $1 \times 10^{-4}$M thymidine.) The cells were then allowed to incubate undisturbed for 144 hours, after which 50 μl of HM, without HAT, but with or without ECGS as appropriate, were added to each well.

Approximately 14 days after fusion, the plates were scored for the presence of growing colonies of hybridomas. Results are as indicated in Table II.

TABLE II

| | Percentage of Wells with Growing Hybridomas, | | | |
|---|---|---|---|---|
| Plate | Wells with Colonies | Wells Plated | ECGS | % Wells w/Col. |
| A | 39 | 96 | – | 40.6 |
| B | 51 | 96 | – | 53.1 |
| C | 30 | 96 | – | 31.3 |
| D | 44 | 96 | + | 45.8 |
| E | 47 | 96 | + | 49.0 |
| F | 40 | 94 | + | 41.2 |

Ave Percentage Colonies/Plate, A–C: 41.6
Ave Percentage Colonies/Plate, D–F: 45.5
Ave Percentage Colonies/Plate, A–F: 43.6

Example 3—Screening of Supernatants for Antibodies

The supernatants from wells with growing colonies of hybridomas were screened using an enzyme-linked immunoassay (EIA). Ninety-six well polystyrene EIA plates were coated with 100 μl/well of 651 conjugated to BSA (651-BSA) for at least two hours at room temperature or 16 hours at 4° C. Unbound material was washed from the wells with five washes of PBS-T and wells then received 50 μl of PBS-T. Fifty μl of supernatant or culture medium alone (negative control) were then added to the wells and allowed to incubate for 30–60 minutes at room temperature. The wells were then washed five times with PBS-T to remove unbound material and each well then received 100 μl of a 1 mg/ml solution of biotinylated anti-mouse IgG (Vector Laboratories, Burlingame, Calif.). The wells were again incubated at room temperature for 30–60 minutes and then washed five times with PBS-T to remove unbound material. Each well then received 100 μl of an avidin biotinylated horseradish peroxidase complex (AB complex; Vector Laboratories. The avidin portion of the AB complex binds with extraordinarily high affinity to the biotin portion of the biotinylated horse anti-mouse IgG, forming a stable, enzyme-containing complex). After an incubation period of 30–60 minutes at room temperature, the unbound reagents were again washed from the wells with PBS-T, and each well received 100 μl of ABTS substrates (K&P). Absorbances (414 nm) were determined 30–60 minutes later using a FLOW Titertek Multiscan 340 EIA Plate reader.

Screening of the hybridoma supernatants revealed two colonies producing antibodies reactive with the coating antigen. These colonies were designated 89-147EH9 and 89-147EC2. These cultures were expanded and cryopreserved and further evaluations were done by competitive inhibition ELISA (enzyme linked immunosorbtive assay) as described below.

Example 4—Competitive Inhibition ELISA (CIEIA)

The supernatants from wells with growing colonies of hybridomas were screened using CIEIA. Ninety-six well polystyrene EIA (enzyme inhibition assay) plates were coated with 100 μl of 651 conjugated to BSA (651-BSA) for at least two hours at room temperature or 16 hours at 4° C. Unbound material was washed from the wells with five washes of PBS-T. The wells then received 50 μl of buffer alone (PBS-T) or inhibitors, either 651 or 573, each diluted to 2 ppm in buffer. The wells then received 50 μl of supernatant from each cell culture, so that each supernatant was reacted with either buffer, 651 or 573 (inhibitors). The combination of equal volumes of supernatants and inhibitors or buffer resulted in a final dilution of the supernatants of 1:2 and a final concentration of inhibitors of 1 ppm. The wells were incubated for 30–60 minutes at room temperature. They were then washed five times with PBS-T to remove unbound material and each well then received 100 μl of a 1 μg/ml solution of biotinylated horse anti-mouse IgG (Vector Laboratories, Burlingame, Calif.), and the assay continued as described for the ELISA, supra.

If the antibodies in a supernatant were reactive with one or both of the inhibitors in solution in the wells, the antibody molecules, or a percentage of the antibody molecules, would bind to the inhibitors, and would therefore form an antibody-inhibitor complex which would stay in solution and be removed from the plate during the washing step. In such a case, the binding of the antibody to the inhibitor would reduce the number of antibody molecules available to bind to the coating antigen, 651-BSA. Because fewer antibody molecules are attached to the 651-BSA, there is a reduction in the number of biotinylated horse anti-mouse IgG molecules bound, resulting in fewer molecules of avidin-peroxidase complex being bound, resulting in reduced hydrolysis of the substrate, leading ultimately to lower absorbances.

It is possible to manipulate the CIEIA to achieve greater inhibition by varying the concentrations of coating antigen, antibodies and detection molecules (such as the horse anti-mouse IgG and the avidin-peroxidase complex). Such "optimization" of the CIEIA is used to obtain higher levels of sensitivity and allow the use of lower concentrations (i.e. higher dilutions) of the monoclonal antibodies.

On test by CIEIA, only cell culture 89-147EH9 was consistently reactive with the coating antigen and inhibitable by compounds 651 and 573. Representative CIEIA data are presented in Table III.

TABLE III

CIEIA of Culture Supernatants

| Culture ID | Supernatant Dilution | Inhibitors (Absorbance) | | |
|---|---|---|---|---|
| | | None | 1 PPM 651 | 1 PPM 573 |
| CF10 | 1:2 | 0.485 | 0.419 | 0.479 |
| EH9 | 1:2 | 0.170 | 0.150 | 0.117 |
| EC2 | 1:2 | 0.847 | 0.652 | 0.520 |
| Culture Medium | | 0.291 | 0.300 | 0.305 |
| EC2 | 1:12 | 0.917 | 0.910 | 0.872 |
| EH9 | 1:2.5 | 0.386 | 0.122 | 0.135 |
| CF10 | 1:2.5 | 0.121 | 0.119 | 0.099 |
| EC2 IB8* | 1:6 | 0.169 | 0.124 | 0.121 |
| Culture Medium | | 0.108 | 0.100 | 0.098 |
| EH9 | 1:4 | 0.515 | 0.186+ | 0.504+ |

*a clone of 89-147EC2.
+tested versus 0.4 ppm of inhibitor.

To demonstrate that the antibodies produced by cell culture 89-147EH9 reacted preferentially with compound 651, a CIEIA was performed as described above, except that the antibody-containing supernatants were reacted with four different inhibitors, each at several different concentrations. The results of this procedure are presented in Table IV. The antibodies in this invention are more strongly reactive with 651 than with the other compounds tested, as evidenced by higher levels of inhibition with 651 than with similar amounts of other biocides.

TABLE IV

CIEIA for Detection of Biocides

| Inhibitor Concentration | 10 Minute Absorbances × 1000 | | | |
|---|---|---|---|---|
| (ppm) | 651 | 573 | NMA | 893 |
| 50 | ND* | 191 | 490 | 516 |
| 10 | 106 | 344 | 518 | 589 |
| 2 | 185 | 504 | 496 | 514 |
| 0.4 | 338 | 461 | 519 | ND |
| 0.08 | 448 | 590 | 429 | ND |
| 0.016 | 491 | ND | ND | ND |
| None | 515, n = 3 | | | |

*ND = not determined
NMA = N-methyl malonamic acid

Example 5—Cloning of Hybridomas

In order to assure that the antibodies reactive with compound 651 were produced by cells of the identical genetic makeup, it was necessary to derive clones of cell culture 89–147EH9. Cloning was accomplished by first determining the total number of viable cells in a population of 89-147EH9 cells. The cell population was then diluted to a density of 4–5 cells per ml of cell culture medium. Two hundred μl of this cell suspension was then planted in each well of four 96 well cell culture dishes, designated I–IV. Fourteen days later, each well was checked by microscopic evaluation for growing colonies of cells. Those with only a single loci of cells were designated monoclonal. The results of the cloning procedure are shown in Table V below.

TABLE V

Cloning of Cell Culture 89-147EH9

| Plate ID | Wells with Colonies | Wells with Single Foci | % With Single Foci |
|---|---|---|---|
| I | 15 | 11 | 73.3 |
| II | 17 | 12 | 70.6 |
| III | 19 | 17 | 89.5 |
| IV | 18 | 13 | 72.2 |
| TOTALS | 17.25 +/ 1.7 | 13.25 +/− 2.6 | 76.4 +/− 8.8 |

Subsequently, each colony was tested for reactivity in the ELISA described previously. Of the colonies, several were selected for expansion and retesting by CIEIA for reactivity with both 651 and 573. Results of this assay are presented in Table VI, below.

TABLE VI

CIEIA: Reactivity of 89-147EH9 Clones-With Compounds 651 and 573

Absorbances × 1000

| Clone ID | PBS | 651 1 PPM | % I* | 573 1 PPM | % I |
|---|---|---|---|---|---|
| IA5 | 528 | 348 | 34.1 | 471 | 10.8 |
| IID1 | 060 | 055 | <1.0 | 057 | <1.0 |
| ID5 | 584 | 429 | 26.5 | 671 | 0.0 |
| IVF12 | 090 | 065 | 27.8 | 073 | 18.9 |
| ID8 | 746 | 807 | 0.0 | 1068 | 0.0 |
| IVE1 | 818 | 452 | 44.7 | 539 | 34.1 |
| IIIH6 | 647 | 471 | 27.2 | 705 | 0.0 |
| IVE4 | 595 | 361 | 39.3 | 539 | 9.4 |
| IVH2 | 680 | 366 | 46.2 | 632 | 7.0 |
| Medium Only | 063 | 059 | <1.0 | 058 | <1.0 |

*% I = percentage inhibition, which is obtained by dividing absorbance obtained with each inhibitor (651 or 573) by the absorbance without inhibition (PBS) and subtracting the quotient from 1 and multiplying the difference by 100. Negative values are expressed as 0.0.

Based on the results of these and subsequent assays, clonal cell line 89-147EH9 IIIH6 was expanded, grown as ascites, purified and used in subsequent assays.

Example 6—Quantitative CIEIA for 651

In order to demonstrate the utility of the CIEIA for determining 651 concentrations in unknown samples, a quantitative immunoassay was developed. This assay is performed as described in Example 4, except that replicate samples of antibody are reacted with a series of known concentrations of compound 651, as well as with several dilutions of samples containing unknown amounts of 651. As described in Example 4, at the highest concentrations of 651, maximal interaction of the antibody with 651 occurs, ultimately leading to reduced absorbance values. Intermediate levels of 651 cause moderate reduction in absorbance values, and low levels of 651 cause little or no reduction in absorbance values.

In the quantitative CIEIA, a standard curve is generated by plotting the absorbance value vs. the log of the concentration of 651. The points are fitted using regression analysis, four parameter logistic curve fitting, or other statistical methods. The concentration of 651 in an unknown sample is then determined by comparing the absorbance values in wells in which the unknown samples were reacted with antibody, to the values obtained for the standard curve.

These procedures were used to estimate the concentrations of 651 in laboratory prepared samples of papermill fluid, cooling tower water and metal working fluid (MWF), all at use dilutions. The results of these assays are presented in Table VII, along with the actual concentrations in the sample. These results indicate that this assay can be used to successfully estimate the level of 651 in a sample.

TABLE VII

Estimates of 651 Concentrations

| Sample | Nominal 651 (ppm)[1] | HPLC (ppm)[2] | CIEIA (ppm)[3] |
|---|---|---|---|
| Papermill | 7.5 | 8.4 | 5.4 |
|  | 2.25 | 2.5 | 3.2 |
|  | 0.375 | 0.41 | 1.3 |
| Cooling Tower | 7.5 | 8.4 | 6.5 |
|  | 2.25 | 2.5 | 2.3 |
|  | 0.375 | 0.41 | 1.3 |
| MWF | 22.5 | 21.2 | 20 |
|  | 11.25 | 9.9 | 11.2 |
|  | 3.75 | 3.3 | 0.74 |

[1] Nominal is the target value for the sample.
[2] HPLC is the standard analytical method currently in use.
[3] CIEIA samples were diluted 1:4 prior to analysis.

A second set of laboratory prepared samples of cooling tower water was analyzed for 651 in duplicate by CIEIA, following the procedure as outlined in Example 4 supra. These results are shown in Table VIII.

TABLE VIII

Estimates of 651 Concentration (ppm) in Cooling Tower Water.

| Nominal | HPLC | CIEIA Single | CIEIA Duplicate |
|---|---|---|---|
| 10 | 9.3 | 10.4 | 11.7 |
| 3 | 2.8 | 3.3 | 6.5 |
| 0.5 | 0.46 | nd* | 0.46 | nd = none detected

Example 7—ELISA Kit

A. Dipstick Format

In the dipstick kit format, a plastic strip is affixed to a vial cap so that it hangs down into a vial. On the surface of the dipstick is a two $cm^2$ detection area to which is affixed 100 ng of anti-651 antibody. The sample is diluted into a vial containing a solution of 651-BSA conjugate (200 ng). The vial cap with the dipstick is screwed onto the vial and incubated for approximately 15–30 minutes. The dipstick is removed and rinsed with water or buffer and screwed onto a vial containing an avidin-HRP (horseradish peroxidase) complex, incubated for 15 min, and then rinsed. The dipstick is then placed in a vial containing HRP substrate such as azino-bis-ethylbenzthiazoline sulfonic acid ("ABTS"). Isothiazolone concentration is then estimated by determining the intensity of the blue color in the vial after a specified incubation period.

B. Membrane Format

The anti-651 antibody is affixed to a membrane and the membrane (approximately two $cm^2$ containing 100 ng antibody) is placed over a small cup. The sample is mixed with the 651-BSA-biotin conjugate (consisting of a 1:2 dilution of the sample, total amount of conjugate is 200 ng) and this solution poured over the membrane. Gravity pulls the solution through the membrane. Next, a solution of avidin-HRP is poured over the membrane, rinsed, and then the detecting solution (HRP substrate) is poured over the membrane. Isothiazolone concentration is then estimated by determining the intensity of the blue color on the membrane.

Example 8—Colorometric Determination of Isothiazolones in Wood

Southern Yellow pine, which had been pressure treated with a solution containing 4,5-dichloro-2-n-octyl-3-isothiazolone using commercial methods, was cut into wafers (0.5×2.5 cm). These wood wafers were soaked in a solution of 3% nonfat milk for 30 minutes. The wafers were then rinsed briefly with PBS-T, and then exposed to the anti-651 antibody, which is covalently linked to horseradish peroxidase at 500 ng/ml, for 15 minutes. The wafers were then washed twice for 30 minutes each in PBS-T buffer. The bound anti-651-HRP complex was visualized by placing the wafers in a vial containing HRP substrate (ABTS). The appearance of a blue color in the solution indicated the presence of 4,5-dichloro-2-n-octyl-3-isothiazolone. A 200 µl aliquot of the solution in the vial was taken and the absorbance determined at 405 nm. This was compared to a control wood wafer treated in an identical manner but containing no isothiazolone. The absorbance values were then corrected for background.

| Sample | $A_{405}$ |
|---|---|
| Control | 0.002 |
| Treated | 0.165 |

These data show that this method could be used for the determination of the isothiazolone concentration in wood or a solid matrix.

We claim:

1. Hybridoma having all of the identifying characteristics of ATCC Patent Deposit B9-14715H9-IIIH6.

2. Antibody produced by a hybridoma of claim 1.

3. A method for determining the presence or concentration of 5-chloro-2-methyl-3-isothiazolone in a specimen comprising bringing said specimen and an antibody according to claim 2 into contact for a period of time sufficient to allow the antibody to specifically binds to 5-chloro-2-methyl-3-isothiazolone to form a complex and thereafter measuring the concentration of said complex thereby determining the presence or concentration of 5-chloro-2-methyl-3-isothiazolone in the specimen.

4. Kit comprising an antibody of claim 2 immobilized on a matrix.

5. Kit according to claim 4 wherein said matrix is a dipstick or a membrane.

* * * * *